United States Patent [19]

Stanley et al.

[11] 3,931,145
[45] Jan. 6, 1976

[54] KETO-AMIDO CONTAINING PHENYLAZOPHENYL DYESTUFFS

[75] Inventors: Lester N. Stanley, Delmar; Russell E. Farris, Elnora, both of N.Y.

[73] Assignee: GAF Corporation, New York, N.Y.

[22] Filed: Dec. 27, 1972

[21] Appl. No.: 319,034

[52] U.S. Cl. ............... 260/207; 260/152; 260/156; 260/158; 260/454; 260/465 D; 260/471 A; 260/471 C; 260/487; 260/488 CD; 260/551 S; 260/556 A; 260/556 AR; 260/558; 260/207.1
[51] Int. Cl.² .................................. C07C 107/06
[58] Field of Search .................... 260/207, 207.1

[56] References Cited
UNITED STATES PATENTS

| | | | |
|---|---|---|---|
| 1,770,714 | 7/1930 | Spengler et al. | 260/207 |
| 2,346,013 | 4/1944 | Dickey | 260/207.1 |
| 2,436,115 | 2/1948 | McNally et al. | 260/207 |
| 3,406,165 | 10/1968 | Kruckenberg | 260/207 |
| 3,553,190 | 1/1971 | Anderton et al. | 260/207 |
| 3,740,189 | 6/1973 | Doss et al. | 260/207 |

FOREIGN PATENTS OR APPLICATIONS

| | | | |
|---|---|---|---|
| 1,200,979 | 9/1965 | Germany | 260/207 |

*Primary Examiner*—Henry R. Jiles
*Assistant Examiner*—Robert W. Ramsuer
*Attorney, Agent, or Firm*—Walter C. Kehm

[57] ABSTRACT

An azo dyestuff containing a benzene coupling component which para to the azo bridge is substituted by a secondary or tertiary amine group containing one or two N-bonded $-C_2H_4CONHC(CH_3)_2CH_2COCH_3$ said dyestuff having the general formula

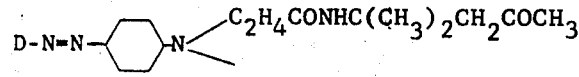

wherein D is the radical of a diazo component and the phenyl ring can be substituted or unsubstituted. These dyestuffs are suitable for dyeing synthetic, particularly polyester fibers. The dyes undergo durable press treatment without obvious loss of fastness properties such as light or ozone fastness.

9 Claims, No Drawings

KETO-AMIDO CONTAINING PHENYLAZOPHENYL DYESTUFFS

This invention relates to dyes which are particularly useful in dyeing polyester fibers, but which may also be employed to dye other synthetic materials such as acetate, triacetate, nylon, polyurethane, and polyacrylonitrile.

Many dyes have been disclosed in the literature and have been manufactured which have certain desirable properties, but most if not all of them are lacking in some very important property.

For example, the dyes of U.S. Pat. No. 3,178,405, as exemplified by the dyestuff having the formula:

(A)

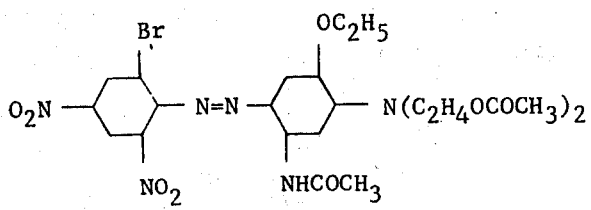

are adversely affected in their fastness properties, especially ozone fastness evidenced by shade change when subjected to durable press treatments, for example, the so-called Korotron resin finish, requiring relatively high curing temperatures.

Likewise, the dyes of U.S. Pat. No. 3,268,507, as exemplified by the compound having the formula:

(B)

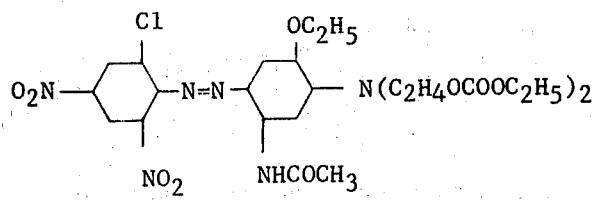

are similarly adversely affected in their fastness properties, when subjected to durable press treatment. The dyes also have a slightly objectionable red flare under artificial light.

A similar deficiency is found after durable press resin treatment in the dyes of U.S. Pat. No. 3,406,165, as exemplified by the compound having the formula:

(C)

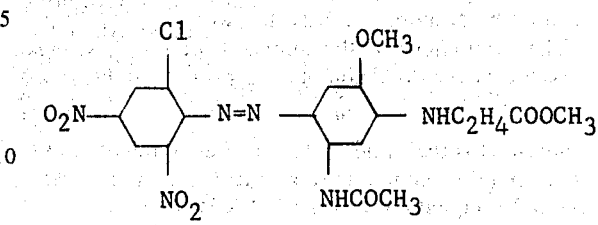

Typical fastness properties which are affected by durable press treatment are light fastness, ozone fastness, shade change and fastness to alkaline perspiration. In particular, a pronounced weakness in fastness to alkaline perspiration is noted in those dyes included within the scope of U.S. Pat. No. 3,406,165.

This same deficiency is also noted in dyes like those of formula (C) which have a terminal unsubstituted amide substituent, e.g. —NHC$_2$H$_4$CONH$_2$. Dyestuffs containing such a terminal substituent are specifically disclosed in U.S. Pat. No. 2,346,013 and are subject to the same deficiency. The latter patent also specifically discloses some dyes containing a terminal substituted amide-containing substituent different from those of the present invention.

It is an object of this invention to provide a dyestuff, and fibrous material dyed therewith, which will not be subject to one or more of the above deficiencies or disadvantages. Another object is the provision of a novel compound suitable for use as the coupling component in such a dyestuff. Other objects and advantages will appear as the description proceeds.

We have now found a class of dyestuffs which have outstanding overall properties. The dyes undergo durable press treatment, e.g. by the Korotron resin treatment, without obvious loss of fastness properties. That is, they withstand durable press resin treatment without objectionable loss of light fastness, ozone fastness, shade change and fastness to perspiration. Furthermore the dyes of this type which are navy in shade do not exhibit red flare, that property wherein a blue dyestuff becomes redder under artificial light. This objectionable red flare is especially noticeable with the dyes of U.S. Pat. No. 3,406,165. Sublimation properties are likewise excellent with the dyes of this invention.

The attainment of the above objects is made possible by the present invention which includes the provision of a compound of the formula:

(I)

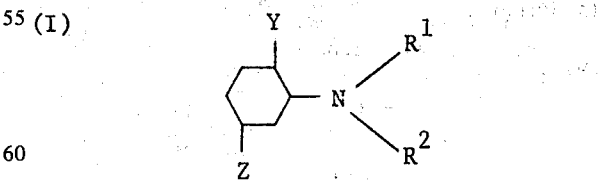

wherein Z is hydrogen, halo, lower alkyl, or NHX; X is SO$_2$R, SO$_2$OR, COR or COOR; R is hydrogen, lower alkyl or phenyl; Y is hydrogen, lower alkyl or lower alkoxy; R$^1$ is C$_2$H$_4$CONHC(CH$_3$)$_2$CH$_2$COCH$_3$; and R$^2$ is R$^1$ or lower alkyl, lower alkenyl or lower alkynyl optionally substituted by chlorine, bromine, fluorine, hydroxy, cyano, thiocyano, lower alkoxy, hydroxyethoxy, polyloweralkyleneoxy, lower alkoxycarbonyl, lower alkanoyloxy, benzoyloxy, or carbamyl optionally substituted by N-mono- or N,N-di-lower alkyl.

The attainment of the above objects is also made possible by the provision of a ddyestuff of the formula:

D—N=N—C$_p$      (II)

wherein D is the radical of a diazo component, and C$_p$ is a coupling component of the formula defined in claim 1 coupled para to the —NR$^1$R$^2$ group.

As employed herein, the term "lower" has reference to a moiety containing about 1 to 4, and preferably 1 or 2, carbon atoms, whereby "alkyl" for example includes methyl, ethyl, propyl, and butyl, "alkenyl" includes allyl and ethenyl, and "alknyl" includes propargyl and acetylene. It will be understood that the H atom in the above —NHX group may if desired be substituted by one of the R$^2$ substituents other than R$^1$, that R$^2$ may be substituted by a quaternary ammonium, pyrridinium, 2-pyrrolidinone, or phthaloylimino group or the like, and that these dyestuffs, or the precursor coupling component, may be readily quaternized by reaction with known alkylating agents such as benzyl chloride, ethyl bromide, ethyl chloride, methyl iodide, dimethylsulfate, ethyl p-toluene sulfonate, and the like.

The compound of formula (I) above may be prepared by reacting a compound of the formula:

(III)

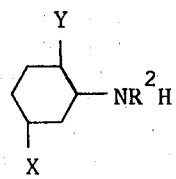

or (IV)

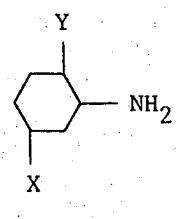

with one or two moles, optionally in each case with up to 10% in excess thereof, of diacetone acrylamide of the formula:

(V)

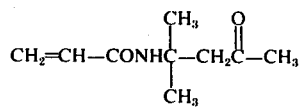

The reaction is generally conducted at elevated temperatures such as about 80° to 115°C. for about 15 to 72 hours, preferably in glacial acetic acid as solvent. To the resulting coupler solution (the acetic acid need not be removed) is added the diazo from the primary amine compound of the formula:

D—NH$_2$      (VI)

The coupling reaction and isolation of the desired dyestuff is carried out in routine, known manner.

Alternatively, a compound of formula (III) or (IV) above may be first coupled with the diazo from the compound of formula (VI) above, and the resulting dyestuff then reacted with one or two moles of the compound of formula (V) above.

According to another method, a compound of the formula:

Hal—C$_2$H$_4$CONHC(CH$_3$)$_2$CH$_2$COCH$_3$      (VII)

wherein Hal is bromine or preferably chlorine, is reacted with a compound of formula (III) or (IV) above, preferably in the presence of an acid binding agent, prior to or after the latter compound (III) or (IV) is coupled with the diazo from the compound of formula (VI).

Although any diazotizable primary aromatic amine compound of formula (VI) above may be employed in preparing the dyestuffs of this invention, a preferred type has the formula:

(VIII)

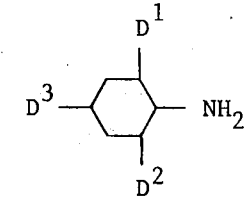

wherein D$^1$ is hydrogen, chlorine, bromine, fluorine, cyano, thiocyano, lower alkylsulfonyl, trifluoromethyl, lower alkoxy, lower alkanoyl, benzoyl, lower alkoxycarbonyl, or carbamyl or sulfamyl optionally substituted by N-mono- or N,N-di-lower alkyl; and D$^2$ and D$^3$ are individually hydrogen, nitro, or one of the D$^1$ substituents.

Another type of compound of formula (VI) which may be employed for the attainment of the desired results has the formula:

(IX)

wherein D$^4$ is hydrogen, halo, cyano, thiocyano, nitro, lower alkyl, loweralkylsulfonyl, trifluoromethyl, lower alkoxy, lower alkanoyl, benzoyl, lower alkoxycarbonyl, or carbamyl or sulfamyl optionally substituted by N-mono- or N,N-di-lower alkyl, and D$^5$ is hydrogen, halo, lower alkoxy, lower alkyl, or nitro.

Examples of the diazo component of formula (VI) above which may be employed in the production of these dyestuffs are as follows:
 p-nitroaniline
 2-chloro-4-nitroaniline
 2,6-dichloro-4-nitroaniline
 6-chloro-2,4-dinitroaniline
 2-bromo-4-nitroaniline
 2,6-dibromo-4-nitroaniline 2-bromo-4-nitroaniline
6-bromo-2,4-dinitroaniline
2-fluoro-4-nitroaniline
2,4,6-trichloroaniline
2-chloro-6-cyano-4-nitroaniline
2-bromo-6-cyano-4-nitroaniline
2-cyano-4-nitroaniline
2-thiocyano-4-nitroaniline
2-nitro-4-thiocyanoaniline
2-methoxy-4-nitroaniline
2,4-di(trifluoromethyl) aniline
2-nitro-4-trifluoromethylaniline
4-nitro-2-trifluoromethylaniline
6-chloro-2-trifluoromethyl-4-nitroaniline
2,6-di(trifluoromethyl)-4-nitroaniline
2-methylsulfonyl-4-nitroaniline
2-ethylsulfonyl-4-nitroaniline
2-chloro-6-methylsulfonyl-4-nitroaniline
2-bromo-6-methylsulfonyl-4-nitroaniline
2,4-di(methylsulfonyl) aniline
6-chloro-2,4-di(methylsulfonyl) aniline
2-carboethoxy-4-nitroaniline
2-sulfamyl-4-nitroaniline
4-sulfamylaniline
2,4-dinitro-6-(dimethylsulfamyl)aniline
2,4-dinitro-6-ethylsulfamylaniline
2-amino-5-nitrobenzenesulfonic acid fluoride
p-aminoacetophenone
p-acetamidoaniline
2-aminobenzothiazole
2-amino-6-chlorobenzothiazole
2-amino-4,6-dichlorobenzothiazole
2-amino-5,6-dichlorobenzothiazole
2-amino-6-bromobenzothiazole
2-amino-6-fluorobenzothiazole
2-amino-6-cyanobenzothiazole
2-amino-6-thiocyanobenzothiazole
2-amino-6-nitrobenzothiazole
2-amino-4,6-dinitrobenzothiazole
2-amino-6-methylbenzothiazole
2-amino-4,6-dimethylbenzothiazole
2-amino-6-methoxybenzothiazole
2-amino-4,7-dimethoxybenzothiazole
2-amino-6-ethoxybenzothiazole
2-amino-5,6-diethoxybenzothiazole
2-amino-6-carboethoxybenzothiazole
2-amino-6-sulfamoylbenzothiazole
2-amino-6-(dimethylsulfamoyl)benzothiazole
2-amino-6-methylsulfonylbenzothiazole
2-amino-6-ethylsulfonylbenzothiazole
2-amino-6-acetylbenzothiazole
2-amino-6-benzoylbenzothiazole Examples of the coupler precursor of formulas (III) or (IV) above which are useful in the preparation of the compounds and dyestuffs of this invention are:
aniline
N-chloroethylaniline
N-hydroxyethylaniline
N-cyanoethylaniline
N-carbomethoxyethylaniline
N-carboethoxyethylaniline
N-ethoxyethylaniline
N-phenoxyethylaniline
N-benzyloxyethylaniline
N-methylcarbamoylethylaniline
N-ethylcarbamoylethylaniline
N-diethylcarbamoylethylaniline
N-(ethylcarbamoyloxyethyl)aniline
N-(dimethylcarbamoyloxyethyl)aniline
N-(phenylcarbamoyloxyethyl)aniline
N-(propoxycarbonylethyl)aniline
N-ethylcarbonyldioxyethylaniline
N-(3-chloro-2-hydroxypropyl)aniline
N-(3-chloro-2-acetoxypropyl)aniline
n-(chloroacetoxyethyl)aniline
m-chloroaniline
N-chloroethyl-m-chloroaniline
m-bromoaniline
N-bromoethyl-m-bromoaniline
o-toluidine
m-toluidine
N-ethyl-m-toluidine
N-cyanoethyl-m-toluidine N-chloroethyl-m-toluidine
N-hydroxyethyl-m-toluidine
o-anisidine
N-methyl-o-anisidine
m-anisidine
N-methyl-m-anisidine
N-ethyl-m-anisidine
N-ethyl-o-phenetidine
m-aminoacetanilide
3'-(N-hydroxyethylamino)acetanilide
3'-(N-cyanoethylamino)acetanilide
3'-(N-ethoxyethylamino)acetanilide
3'-(ethylamino)acetanilide
3'-(ethylamino)benzanilide
3'-amino-4'-methoxyacetanilide
3'-amino-4'-ethoxyacetanilide
3'-(ethylamino)-4'-methoxyacetanilide
3'-(cyanoethylamino)-4'-methoxyacetanilide
3'-(hydroxyethylamino)4'-methoxyacetanilide
3'-(methoxyethylamino)-4'-methoxyacetanilide
3'-(N-methylcarbamoylethylamino)4'-methoxyacetanilide
3'-(N-ethylcarbamoyloxyethylamino)-4'-methoxyacetanilide
3'-(N-dimehtylcarbamoyloxyethylamino)-4'-methoxyacetanilide
3'-(N-propoxycarbonylethylamino)-4'-methoxyacetanilide
3'-(N-ethylcarbonyldioxyethylamino)-4'-methoxyacetanilide
3'-(N-3-chloro-2-hydroxypropylamino)-4'-methoxyacetanilide
3'-(N-3-chloro-2-acetoxypropylamino)-4'-methoxyacetanilide
3'-(N-chloroacetoxyethylamino)-4'-methoxyacetanilide
3'-(ethylamino)-4'-ethoxyacetanilide The dyestuffs of this invention are of the disperse type, being sparingly to non-soluble in water, and are generally applied to fibrous material by the disperse method with the aid of the known dispersing agents, wetting agents and/or thickeners and the like. The Thermosol method of dyeing is preferable, involving padding the fibrous material with an aqueous dispersion of the dyestuff at elevated temperatures of about 140°–190°F., squeezed to a liquor: fiber ratio of about 0.5–1.5;1, dried, and cured at the usual temperatures of for example about 350°–450°F.

The fibrous material suitable for coloration with these dyestuffs may be in any form such as woven, knot or felt fabrics, staple, filament, yarn, tow, or skein or the like, and may have a basis of cellulose acetate or triacetate, polyamide such as nylon 66, polyolefin such as polypropylene, polyacrylonitrile such as Orlon or modified versions thereof, or other synthetic organic polymer, preferably polyester such as Dacron polyethylene terephthalate, along or admixed with natural fibers such as cotton or other cellulose forms, silk, wool, or the like.

The following examples illustrate the invention and are not limitative. All parts and proportions referred to herein and in the appended claims are by weight unless otherwise indicated.

EXAMPLE 1

Preparation of the coupling component having the formula:

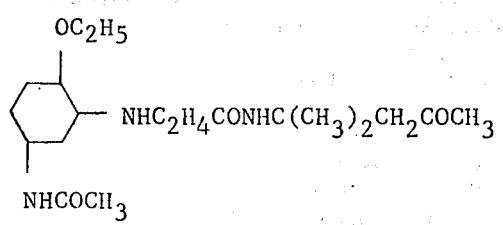

38.8 g. (0.2 mole) 5-acetamido-o-phenetidide are dissolved in 100 ml. glacial acetic acid. 37 g. (0.22 mole) diacetone acrylamide are added. After solution in glacial acetic acid it is heated to 85°C. The reaction is followed by thin layer chromatography (TLC). After 8 hours at 85°C. about 80% of the starting free amine has been converted to the monosubstituted product. An additional 3.7 g. (10%) diacetone acrylamide are added. After another 8 hours at 85°C. about 90% of the product is monosubstituted. Another 3.7 g. diacetone acrylamide are added. After another 8 hours at 85°C. no free amine remains.

EXAMPLE 2

Preparation of the dyestuff having the formula:

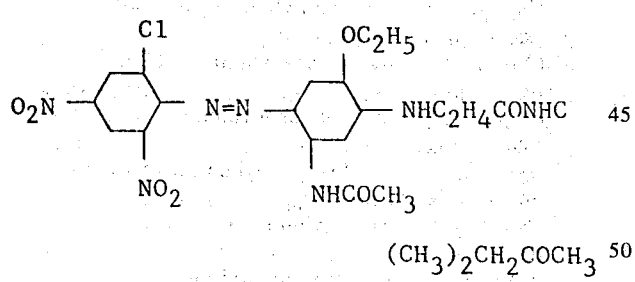

The diazonium salt of 6-chloro-2,4-dinitroaniline is prepared in known manner by dissolving 21.7 g. (0.1 mole) in 105 g. sulfuric acid 66°Be. It is stirred 2 hours. To this is added slowly 0.1 mole nitrosyl sulfuric acid (prepared by dissolving 6.9 g. sodium nitrile in 100 g. sulfuric acid 100%). The diazo is stirred 2 hours and then added slowly (dropwise) to a cold coupler solution consisting of one half the solution of Example 1 to which has been added 20 ml. hydrochloric acid 20°Be. and 600 ml. water. The pH is raised to 5–6 with sodium acetate. The precipitated product was filtered, washed with water and dried. 45.9 g. (77%) of dyestuff are obtained. It dyes polyester a rich navy blue.

EXAMPLE 3

Preparation of a coupler product having the formula:

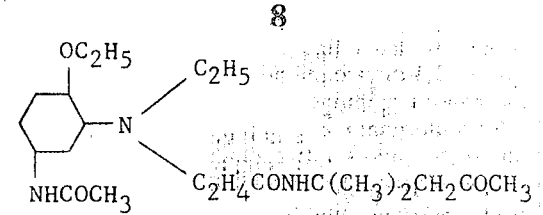

A diacetone acrylamide product is prepared as in Example 1. The acetic acid is neutralized with 70 ml. sodium hydroxide (30% by weight) to pH 6. The amorphous material is dissolved in 250 ml. isopropanol and heated to 85°C. 28 g. (0.22 mole) diethylsulfate is added slowly over a 2 hour period. A pH 5.0–6.0 is maintained by addition of barium carbonate. The reaction is followed by TLC. Heating is continued at 85°C. for 72 hours making 5 g. additions of diethyl sulfate approximately every 8 hours and maintaining a pH of 5.0–6.0 with barium carbonate. At the end of this time TLC shows that all of the monosubstituted product has been converted into a disubstituted product.

EXAMPLE 4

Preparation of the dyestuff having the formula:

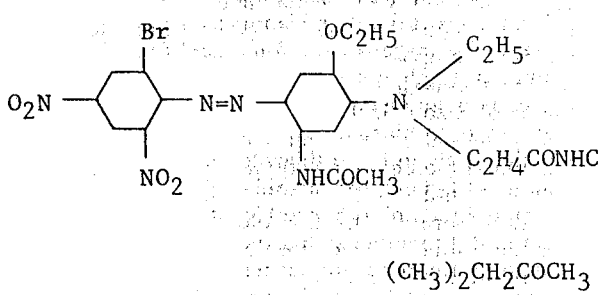

In a manner similar to Example 2, 26.2 g. (0.1 mole) 6-bromo-2,4-dinitroaniline are diazotized and coupled. The coupler is prepared by adding to ½ of the solution of Example 3 (0.1 mole), 500 ml. water and 10 ml. hydrochloric acid 20°Be. and cooling in an ice bath. The diazo is added dropwise over a 1 hour period. Sodium acetate is added near the end of the coupling to insure completeness of the reaction. The product is filtered, washed neutral and dried. 55.5 g. dry dyestuff are obtained (84). It dyes polyester fiber a greenish-blue shade.

EXAMPLE 5

Preparation of the coupling component having the formula:

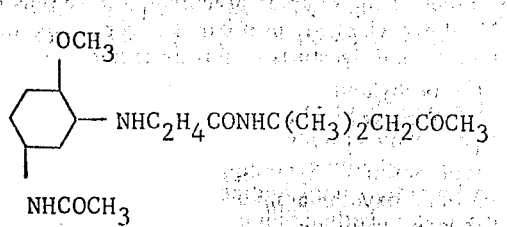

In the manner of Example 1, 72 g (0.4 mole) 2-amino-4-acetanisidide are dissolved in 200 ml. glacial acetic acid along with 74 g. diacetone acrylamide (0.44 mole). The reaction mix is heated at 85°C. for 24 hours with 10% increment additions of diacetone acrylamide until TLC shows the free amine to have disappeared.

EXAMPLE 6

Preparation of the dyestuff having the formula:

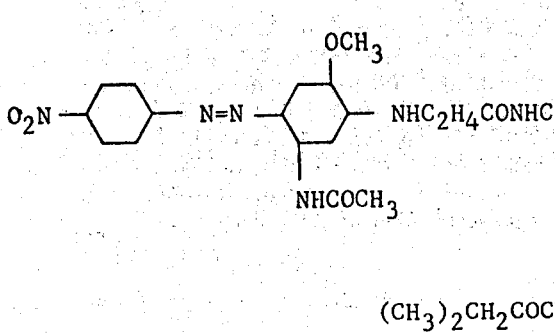

13.8 g. (0.1 mole) p-nitroaniline are diazotized in known manner. The diazo solution is added dropwise to a solution of the coupler prepared by dissolving ¼ of the product of Example 5 (0.1 mole) in 25 ml. hydrochloric acid 20° Be. and 500 ml. water, and cooling in an ice bath. Sodium acetate is added to insure completeness of coupling. The product is filtered, washed neutral and dried. 33.7 g (68%) dyestuff are obtained which dyes polyester deep red-violet shades.

EXAMPLE 7

Preparation of a coupling component having the formula:

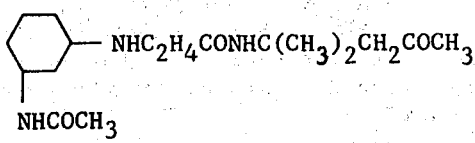

In a manner similar to Example 1, 90 g. 3-aminoacetanilide (0.6 mole), as the HCl salt, dissolved in 450 ml. glacial acetic acid. 50 g. soldium acetate are added. 111.6 g. diacetone acrylamide (0.66mole) are added and heated at 100°C. for 24 hours with 10% increment additions of diacetone acrylamide until TLC shows no free amine.

EXAMPLE 8

Preparation of the dyestuff having the formula:

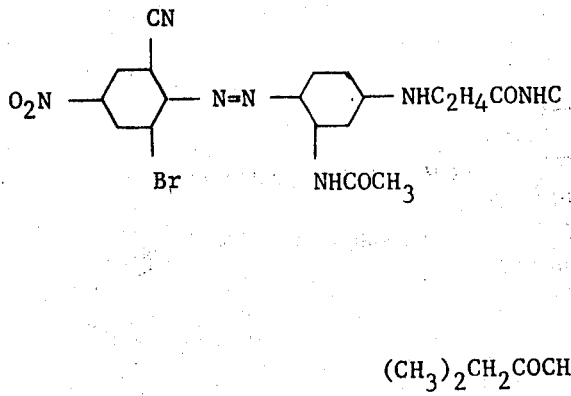

24.2 g. 2-Bromo-6-cyano-4-nitroaniline (0.1 mol are diazotized using nitrosyl sulfuric acid in the mann of Example 2. The diazo solution is added to 1/6 tl product of Example 7 (0.1 mole) which is dissolved 25 ml. hydrochloric acid 20°Be. and 500 ml. wat cooled in an ice bath. 32 g. product are obtained whi( dyes polyester fiber in medium blue shades.

EXAMPLE 9

Preparation of the coupling component having tl formula:

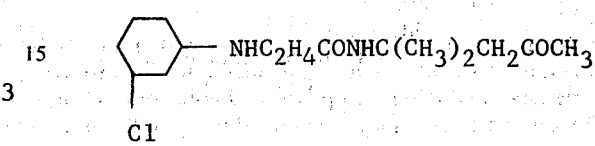

In a manner similar to Example 1, 127.5 g. m-chlor( aniline (1.0 mole) are dissolved in 500 ml. glaci acetic acid. 185.9 g. diacetone acrylamide are adde and the charge heated at 100°C. for 24 hours. No add tional diacetone acrylamide is necessary.

EXAMPLE 10

Preparation of the dyestuff having the formula:

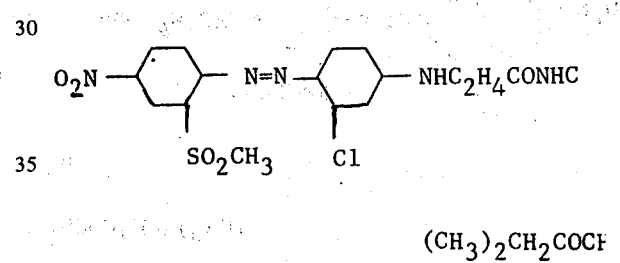

In the manner of Example 2, 21.6 g. (0.1 mole) ' methylsulfonyl-4-nitroaniline are diazotized using n trosyl sulfuric acid. This is added dropwise to 1/10 tr produce of Example 9 which has been dissolved in 10 ml. glacial acetic acid, 200 ml. water, and cooled in a ice bath. After filtering, washing and drying, 25.6 ; (50%) product are obtained. The product dyes polye ter in reddish-brown shades.

EXAMPLE 11

Preparation of the coupling component having tr formula:

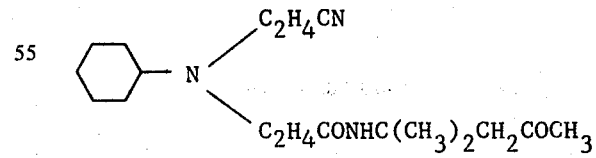

In the manner of Example 1, 146 g. N-cyanoethylan line (1.0 mole), 500 ml. glacial acetic acid and 169 diacetone acrylamide are heated together at 100°C. f( 24 hours with 10% diacetone acrylamide incremen added until TLC shows disappearance of free amine

EXAMPLE 12

Preparation of a dyestuff having the formula:

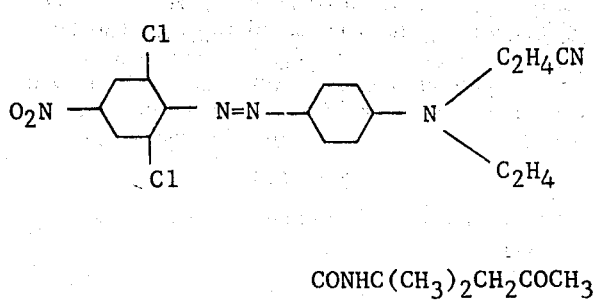

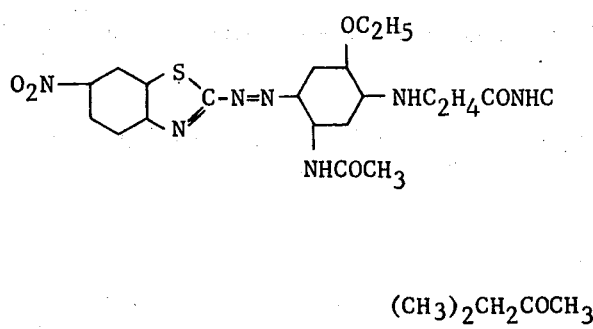

In the manner of Example 2, 20.7 g. 2,6-dichloro-4-nitroaniline (0.1 mole) are diazotized with nitrosyl sulfuric acid, and added dropwise to a cold solution of 1/10 Example 11 (0.1 mole) dissolved in 300 ml. water. After filtering, washing and drying 35 g. product (66%) are obtained which dyes polyester fiber in yellow-brown shades.

EXAMPLE 13

Preparation of the dyestuff having the formula:

A hot (95°C.) solution of 19.5 g. 2-amino-6-nitrobenzothiazole (0.1 mole) in 400 ml. glacial acetic acid is added dropwise to a mixture of 120 g. glacial acetic acid and 100 g. nitrosyl sulfuric acid at 15–20°C. The mass is stirred 1½ hours. This dark orange diazo solution is added slowly over a ½ hour period to a solution equivalent to the glacial acetic acid solution of 0.1 mole of the coupler of Example 1. This mixture is stirred in an ice bath 2 hours, and then drowned into 5.1 ice water to yield 38 g. product (67%). The product dyes polyester fiber bright violet shades.

EXAMPLE 14

Preparation of the dyestuff having the formula:

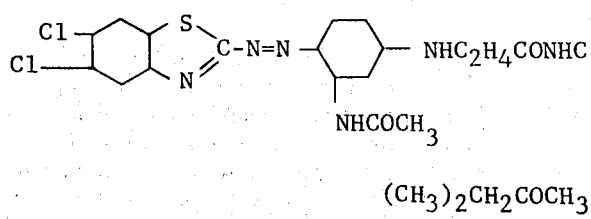

In the manner of Example 13, 21.9 g. 5,6-dichloro-2-aminobenzothiazole (0.1 mole) are added to 400 ml. glacial acetic acid and diazotized with nitorsyl sulfuric acid. This is added slowly to a cold solution of 0.1 mole coupler of Example 7 to yield 38 g. (69%) of a product which dyes polyester fiber a bright red shade.

The dye components shown in the following table are reacted in a manner similar to the above to produce dyestuffs and results in accordance with this invention, as indicated.

TABLE

| Ex. | Diazo Base | Coupler | Shade |
|---|---|---|---|
| 15 | 2-Chloro-4-nitroaniline | ⌬—NHC₂H₄CONHC(CH₃)₂CH₂COCH₃ <br> NHCOCH₃ | Red |
| 16 | 2-Cyano-4-nitroaniline | Do | Rubine |
| 17 | Sulfanilamide | Do | Orange |
| 18 | 2-Methylsulfonyl-4-nitroaniline | Do | Pink |
| 19 | 2-Bromo-6-cyano-4-nitroaniline | | Salmon |
| 20 | 2-Chloro-4,6-dinitroaniline | ⌬—NHC₂H₄CONHC(CH₃)₂CH₂COCH₃ <br> Cl | Blue |
| 21 | 2-Cyano-4-nitroaniline | Do (OC₂H₅ / N(C₂H₅)(C₂H₄CONHC(CH₃)₂CH₂COCH₃) / NHCOCH₃) | Red Violet |
| 22 | 2-Chloro-4,6-dinitroaniline | | Blue |

(Note: for Ex. 15, the formula expressed in LaTeX-like form: $NHC_2H_4CONHC(CH_3)_2CH_2COCH_3$ with $NHCOCH_3$ substituent)

TABLE-continued

| Ex. | Diazo Base | Coupler | Shade |
|-----|------------|---------|-------|

Coupler structure (above examples 23-28):
Cyclohexane with OCH₃, NHCOCH₃, and $NHC_2H_4CONHC(CH_3)_2CH_2COCH_3$ substituents.

| Ex. | Diazo Base | Coupler | Shade |
|-----|------------|---------|-------|
| 23 | 2-Bromo-4,6-dinitroaniline | Do | Blue |
| 24 | 2,6-Dichloro-4-nitroaniline | Do | Gray Violet |
| 25 | 2-Bromo-4,6-dinitroaniline | Do | Blue |
| 26 | 2-Bromo-6-cyano-4-nitroaniline | Do | Greenish Blue |
| 27 | p-nitroaniline | Do | Red Violet |
| 28 | 2-chloro-4-nitroaniline | Do | Violet |
| 29 | p-nitroaniline | | Orange |

Coupler structure (examples 29-32): Cyclohexane-N with $C_2H_4CN$ and $C_2H_4CONHC(CH_3)_2CH_2COCH_3$.

| 30 | p-aminoacetophenone | Do | Yellow |
| 31 | 2-Chloro-4-nitroaniline | Do | Red Orange |
| 32 | 2-Trifluoromethyl-4-nitroaniline | Do | Red |
| 33 | p-nitroaniline | | Orange |

Coupler structure (examples 33-37): Cyclohexane-N with $C_2H_4OCOCH_3$ and $C_2H_4CONHC(CH_3)_2CH_2COCH_3$.

| 34 | 2-Chloro-4-nitroaniline | Do | Red Orange |
| 35 | 2-Cyano-4-nitroaniline | Do | Red |
| 36 | 2-Chloro-4,6-dinitroaniline | Do | Violet |
| 37 | p-cyanoaniline | Do | Orange |
| 38 | 2-Chloro-4-nitroaniline | | Rubine |

Coupler structure (examples 38-41): Cyclohexane with NHCOCH₃ and N($C_2H_4OCOCH_3$)($C_2H_4CONHC(CH_3)_2CH_2COCH_3$).

| 39 | 2,6-Dichloro-4-nitroaniline | Do | Red Brown |
| 40 | 2-Bromo-6-cyano-4-nitroaniline | Do | Blue Violet |
| 41 | 2-Amino-5,6-dichlorobenzothiazole | | Pink |

Coupler structure (examples 41-43): Cyclohexane with NHCOCH₃ and $NHC_2H_4CONHC(CH_3)_2CH_2COCH_3$.

| 42 | 2-Amino-6-nitrobenzothiazole | Do | Violet |
| 43 | 2-Amino-5,6-dichlorobenzothiazole | | Blue Violet |

Coupler structure (examples 43-45): Cyclohexane with OCH₃, NHCOCH₃, and $NHC_2H_4CONHC(CH_3)_2CH_2COCH_3$.

| 44 | 2-Amino-6-ethoxybenzothiazole | Do | Blue Violet |
| 45 | 2-Amino-5,6-dichlorobenzothiazole | | Pink |

Coupler structure (examples 45-47): Cyclohexane with Cl and $NHC_2H_4CONHC(CH_3)_2CH_2COCH_3$.

| 46 | 2-Amino-6-nitrobenzothiazole | Do | Violet |
| 47 | 2-Amino-6-chlorobenzothiazole | | Orange |

Coupler structure (examples 47-49): Cyclohexane-N with $C_2H_4CN$ and $C_2H_4CONHC(CH_3)_2CH_2COCH_3$.

| 48 | 2-Amino-6-nitrobenzothiazole | Do | Red Violet |
| 49 | 2-Chloro-4-nitroaniline | | Red Orange |

Coupler structure: Cyclohexane with CH₃ and $NHC_2H_4CONHC(CH_3)_2CH_2COCH_3$.

TABLE-continued

| Ex. | Diazo Base | Coupler | Shade |
|---|---|---|---|
| 50 | 2-Cyano-4-nitroaniline | Do | Red Orange |
| 51 | 2,6-Dichloro-4-nitroaniline | Do | Red Brown |
| 52 | 2-Amino-5,6-dichlorobenzothiazole | Do | Red |
| 53 | 2-Chloro-4-nitroaniline | Do | Red |

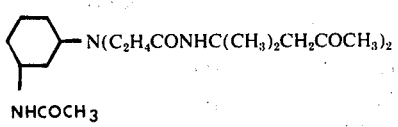

EXAMPLE 54

The dyestuff of Example 2 is dispersed to a 13% active paste in a Vibro Energy Mill using Tamol SN (sodium salt of condensed naphthalenesulfonic acid, Rohm and Hass Co.) and Marasperse CB (partially desulfonated sodium lignosulfonate, Am. Can co.).

About 2 oz. of this dispersed dyestuff are dispersed in 83 cc. warm water and poured into a solution containing 0.2 g. Keltex gum (alginic thickening agent), and 1 cc. Nekal NF (sodium alkylnaphthalenesulfonate, GAF Corp.). This dispersion or solution is made up to a gallon with water.

Dacron polyester material is padded with the above dyebath at 160°F., dried and cured at 425°F. for 90 seconds. The material is soaped at the boil for 5 minutes, washed and dried. A rich navy blue coloration is obtained which has excellent light fastness. After Korotron permanent press treatment, the dyeings maintain excellent light fastness, no shade change and excellent fastness to alkaline and acid perspiration. Another advantage is lack of red flare under artificial light.

This invention has been disclosed with respect to certain preferred embodiments, and it will be understood that modifications and variations thereof will become obvious to persons skilled in the art and are intended to be included within the spirit and purview of this application and the scope of the appended claims.

We claim:

1. A dyestuff of the formula:

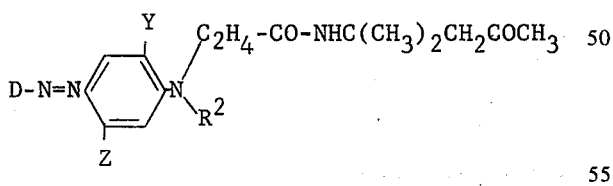

wherein
D is (a) phenyl or phenyl substituted with a substituent selected from the group of chlorine, bromine, fluorine, cyano, thiocyano, lower alkylsulfonyl, nitro, trifluoromethyl, lower alkoxy, lower alkanoyl, benzoyl, lower alkoxycarbonyl, unsubstituted carbamyl, unsubstituted sulfamyl, and carbamyl or sulfamyl N-mono-or N, N-di- substituted with lower alkyl
Z is hydrogen, halogen, lower alkyl or NHX and X is $SO_2$—R, $SO_2OR$, COR or COOR with R being hydrogen, phenyl or lower alkyl;
Y is hydrogen, lower alkyl or lower alkoxy
$R^2$ is $C_2H_4$—CO—$NHC(CH_3)_2CH_2COCH_3$, hydrogen, lower alkyl, lower alkenyl, lower alkynyl or lower alkyl, lower alkenyl or lower alkynyl substituted with chlorine, bromine, fluorine, hydroxy, cyano, thiocyano, lower alkoxy, hydroxyethoxy, polyloweralkyleneoxy, lower alkoxycarbonyl, lower alkanoyloxy, benzoyloxy, unsubstituted carbamyl, or carbamyl N-mono- or N,N-di- substituted with lower alkyl.

2. A dyestuff as defined in claim 1 wherein D is derived from a compound of the formula:

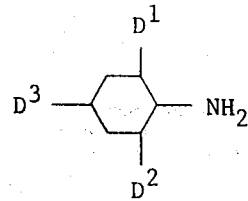

wherein
$D^1$ is
hydrogen, chlorine, bromine, fluorine, cyano, thiocyano, lower alkylsulfonyl, trifluoromethyl, lower alkoxy,
lower alkanoyl, benzoyl, lower alkoxycarbonyl unsubstituted carbamyl, unsubstituted sulfamyl, or
carbamyl or sulfamyl substituted by N-mono- or N,N-di-lower alkyl; and
$D^2$ and $D^3$ are individually
hydrogen,
nitro, or
one of the $D^1$ substituents.

3. A dyestuff as defined in claim 1 wherein $R^2$ is $C_2H_4CONHC(CH_3)_2CH_2 COCH_3$ 4. A dyestuff as defined in claim 1 having the formula:

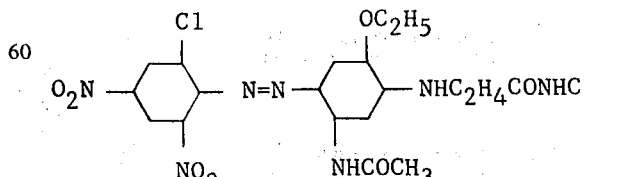

$(CH_3)_2CH_2COCH_3$

5. A dyestuff as defined in claim 1 having the formula:
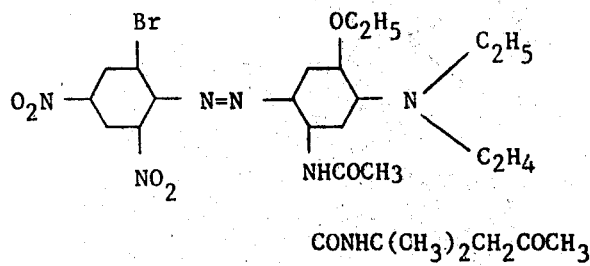
6. A dyestuff as defined in claim 1 having the formula:
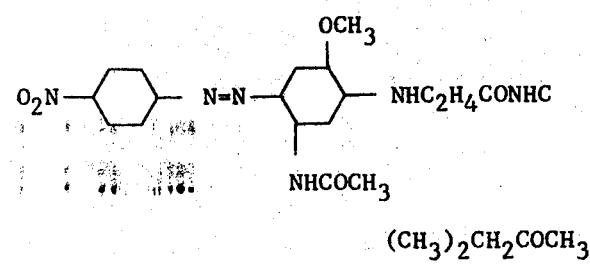
7. A dyestuff as defined in claim 1 having the formula:
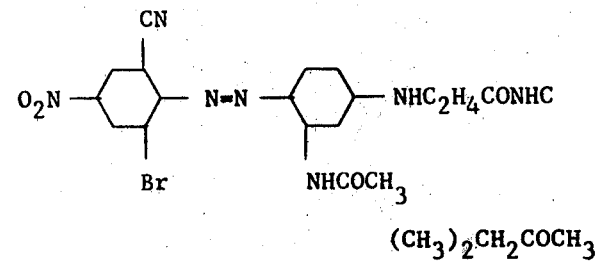
8. A dyestuff as defined in claim 1 having the formula:
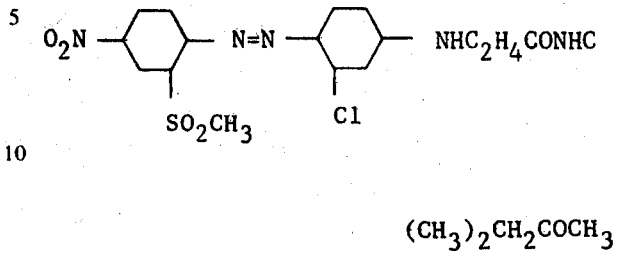
9. A dyesuff as defined in claim 1 having the formula:
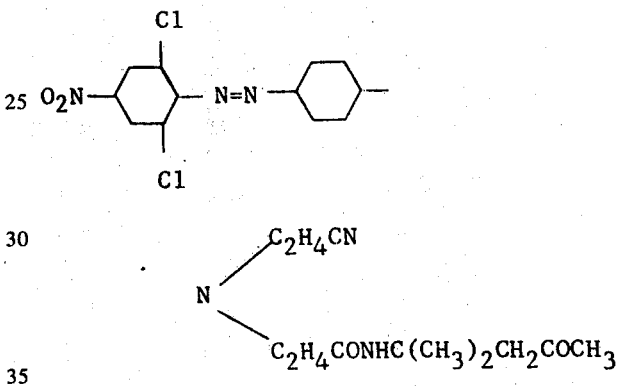
* * * * *